(12) United States Patent
Benzel et al.

(10) Patent No.: US 9,149,227 B2
(45) Date of Patent: *Oct. 6, 2015

(54) DETECTION AND CHARACTERIZATION OF HEAD IMPACTS

(75) Inventors: Edward C. Benzel, Gates Mills, OH (US); Vincent J. Miele, Bridgeport, WV (US); Adam J. Bartsch, Lakewood, OH (US); Lars G. Gilbertson, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 176 days.

This patent is subject to a terminal disclaimer.

(21) Appl. No.: 13/184,385

(22) Filed: Jul. 15, 2011

(65) Prior Publication Data

US 2012/0143526 A1 Jun. 7, 2012

Related U.S. Application Data

(60) Provisional application No. 61/364,639, filed on Jul. 15, 2010, provisional application No. 61/444,281, filed on Feb. 18, 2011.

(51) Int. Cl.
| | |
|---|---|
| *G06F 19/00* | (2011.01) |
| *G01N 3/30* | (2006.01) |
| *A61B 5/00* | (2006.01) |
| *A42B 3/04* | (2006.01) |
| *A61B 5/11* | (2006.01) |

(52) U.S. Cl.
CPC .................. *A61B 5/682* (2013.01); *A42B 3/046* (2013.01); *A61B 5/1121* (2013.01); *A61B 5/7264* (2013.01); *A61B 5/6803* (2013.01); *A61B 5/7267* (2013.01)

(58) Field of Classification Search
CPC ...... A42B 3/046; A61B 5/1121; A61B 5/682; A61B 5/7264; A61B 5/7267; A61B 5/6803
USPC ............... 702/41, 42, 141; 345/440, 473, 619
See application file for complete search history.

(56) References Cited

U.S. PATENT DOCUMENTS

| | | | |
|---|---|---|---|
| 5,539,935 | A | 7/1996 | Rush, III |
| 5,621,922 | A | 4/1997 | Rush, III |

(Continued)

FOREIGN PATENT DOCUMENTS

| | | | |
|---|---|---|---|
| JP | 06-174740 A | | 6/1994 |
| JP | 06174740 A | | 6/1994 |

(Continued)

OTHER PUBLICATIONS

Svein Kleiven, "Correlation of an FE Model of the Human Head with Local Brain Motion—Consequences for Injury Prediction", Stapp Car Crash Journal, vol. 46 (Nov. 2002), pp. 123-144, hereinafter 'Kleiven'.*

(Continued)

*Primary Examiner* — Alexander Satanovsky
(74) *Attorney, Agent, or Firm* — Tarolli, Sundheim, Covell & Tummino LLP

(57) ABSTRACT

Systems and methods are provided for determining an acceleration at a location of interest within one of a user's head and neck. At least one of linear acceleration data, angular acceleration data, angular velocity data, and orientation data is produced using at least one sensing device substantially rigidly attached to an ambient-accessible surface of the user's head. The location of interest is represented relative to a position of the at least one sensing device as a time-varying function. An acceleration at the location of interest is calculated as a function of the data produced at the sensing device and the time-varying function representing the location of interest. The calculated acceleration at the location of interest is provided to at least one of the user and an observer in a human-perceptible form.

28 Claims, 6 Drawing Sheets

(56) References Cited

U.S. PATENT DOCUMENTS

| | | | |
|---|---|---|---|
| 5,978,972 A | | 11/1999 | Stewart et al. |
| 6,909,221 B2* | | 6/2005 | Ayazi et al. .................. 310/321 |
| 6,925,851 B2 | | 8/2005 | Reinbold et al. |
| 6,941,952 B1* | | 9/2005 | Rush, III ...................... 128/861 |
| 7,384,380 B2 | | 6/2008 | Reinbold et al. |
| 2002/0139376 A1* | | 10/2002 | Waddy ........................ 128/861 |
| 2003/0217582 A1 | | 11/2003 | Reinbold et al. |
| 2005/0100873 A1* | | 5/2005 | Meythaler et al. ........... 434/267 |
| 2005/0117929 A1 | | 6/2005 | Jung et al. |
| 2005/0177335 A1 | | 8/2005 | Crisco, III et al. |
| 2005/0177929 A1* | | 8/2005 | Greenwald et al. ............... 2/425 |
| 2006/0047447 A1 | | 3/2006 | Brady et al. |
| 2006/0074338 A1 | | 4/2006 | Greenwald et al. |
| 2006/0189852 A1* | | 8/2006 | Greenwald et al. ........... 600/300 |
| 2006/0192367 A1* | | 8/2006 | Zumpano .................. 280/730.1 |
| 2007/0287596 A1 | | 12/2007 | Case, Jr. et al. |
| 2008/0269579 A1 | | 10/2008 | Schiebler |
| 2008/0306707 A1* | | 12/2008 | Vock et al. .................... 702/141 |
| 2009/0000377 A1* | | 1/2009 | Shipps et al. ............... 73/514.16 |
| 2011/0227825 A1* | | 9/2011 | Liberty et al. ................ 345/158 |
| 2012/0142270 A1 | | 6/2012 | Abolfathi et al. |

FOREIGN PATENT DOCUMENTS

| | | |
|---|---|---|
| JP | 2002-141841 A | 5/2002 |
| JP | 2002141841 A | 5/2002 |
| KR | 10-2002-0045720 A | 6/2002 |
| KR | 2002-0045720 | 6/2002 |
| KR | 10-2003-0093735 A | 12/2003 |
| KR | 2003-0093735 | 12/2003 |
| WO | WO-99/10052 A1 | 3/1999 |
| WO | WO-02/066118 A1 | 8/2002 |
| WO | WO-03/063119 A2 | 7/2003 |
| WO | WO-2005/077115 A2 | 8/2005 |

OTHER PUBLICATIONS

Richard M. Greenwald et al., "Head Impact Severity Measures for Evaluating Mild Traumatic Brain Injury Risk Exposure", Neurosurgery, Issue: vol. 62(4), Apr. 2008, p. 789-798.*

"Conservation of Angular Momentum in Impact", 2003, p. 1 of 6, http://physics.bu.edu/ulab/intro1/angularmo.pdf.*

Marike J. van der Horst, "Human Head Neck Response in Frontal, Lateral and Rear End Impact Loading", by Eindhoven: Technische Universiteit Eindhoven, 2002, 217 pp., http://alexandria.tue.nl/extra2/200211336.pdf.*

Liying Zhang et al., "A proposed Injury Threshold for Mild Traumatic Brain Injury", Transaction of the ASME, vol. 126, Apr. 2004, pp. 226-236, http://www.x2impact.com/X2_SBI_INFO_files/JBENDY_126_2_226_1.pdf.*

Michael Higgins et al. "Measurement of Impact Acceleration: Mouthpiece Accelerometer Versus Helmet Accelerometer", Journal of Athletic Training 2007;42(1), pp. 5-10.*

PCT Int'l Search Report and Written Opinion dated Feb. 27, 2012 for PCT Int'l Appln. No. PCT/US2011/044251, filed Jul. 15, 2011, pp. 1-10.

Chou et al., "On the Kinematics of the Head Using Linear Acceleration Measurements", *J. Biomechanics*, 9:607-613 (1976).

Rowson et al., "Six Degree of Freedom Head Acceleration Measurements in Football Players", *Injury Biomechanics Research*, Proceedings of the 35th International Workshop, 85-92 (undated) (Abstract).

Crisco et al., "An Algorithm for Estimating Acceleration Magnitude and Impact Location Using Multiple Nonorthogonal Single-Axis Accelerometers", *Journal of Biomechanical Engineering*, 126:849-854 (2004).

Pages i through 45 of the MSc Thesis of Sarah J. Manoogian, submitted to the faculty of the Virginia Polytechnic Institute and State University entitled "Analysis of Linear Head Accelerations from Collegiate Football Impacts" (2005).

Miele et al., "Objectifying When to Halt a Boxing Match: A Video Analysis of Fatalities", *Neurosurgery*, 60:307-316 (2007).

Olvey et al., "The Development of a Method to Measure Head Acceleration and Motion in High-Impact Crashes", *Neurosurgery*, 54:672-677 (2004).

Takhounts et al., "Analysis of 3D Rigid Body Motion Using the Nine Accelerometer Array and the Randomly Distributed In-Plane Accelerometer Systems" Website: www-nrd.nhtsa.dot.gov/pdf/esv/esv21/09-0402.pdf, undated, pp. 1-10.

Viano et al., "Concussion in Professional Football: Comparison with Boxing Head Impacts—Part 10", *Neurosurgery*, 57:1154-1172 (2005).

* cited by examiner

DETECTION AND CHARACTERIZATION OF HEAD IMPACTS

RELATED APPLICATIONS

This application claims priority from each of U.S. Provisional Application No. 61/364,639, filed Jul. 15, 2010 and U.S. Provisional Application No. 61/444,281, filed Feb. 18, 2011. The subject matter of both applications is incorporated herein by reference.

FIELD OF THE INVENTION

The present invention relates to systems and methodologies for diagnosis of medical conditions, and, in particular, is directed to systems and methods for detecting and characterizing head impacts.

BACKGROUND OF THE INVENTION

There are over forty-seven million athletes under the age of twenty-four who participate in contact sports like football, basketball, hockey, soccer, boxing, and mixed martial arts (MMA) each year in the United States. Each of these young athletes is at risk for concussive traumatic brain injuries (cTBI) and long-term brain dysfunction due to repeated head impact. These young athletes, with developing neurological systems, sustain a large portion of the 3.8 million cTBI occurring yearly and are at heightened risk of developing deleterious long-term neurological, physiological and cognitive deficits. The head impact conditions responsible for cTBI and potential long-term deficits in athletes are unknown.

SUMMARY OF THE INVENTION

In accordance with an aspect of the present invention, a method is provided for determining an acceleration at a location of interest within one of a user's head and neck. At least one of linear acceleration data, angular acceleration data, angular velocity data, and orientation data is produced using at least one sensing device substantially rigidly attached to an ambient-accessible surface of the user's head. The location of interest is represented relative to a position of the at least one sensing device as a time-varying function. An acceleration at the location of interest is calculated as a function of the data produced at the sensing device and the time-varying function representing the location of interest. The calculated acceleration at the location of interest is provided to at least one of the user and an observer in a human-perceptible form.

In accordance with another aspect of the present invention, a system is provided for characterizing an impact to a user. A sensor assembly is configured to measure at least one of the linear acceleration, angular velocity, angular acceleration, and orientation of the sensor assembly. A data transform component is operatively connected to the sensor assembly and configured to represent a location of interest in one of the head and the neck of the user relative to a position of the sensor assembly as a time-varying function. The data transform component is further configured to calculate an acceleration at the location of interest from the measured at least one of the linear acceleration, angular velocity, angular acceleration, and orientation of the sensor assembly and the time-varying function representing the location of interest. A system interface is configured to provide the calculated acceleration at the location of interest to a user in a human-perceptible form.

In accordance with another aspect of the present invention, a system is provided for characterizing an impact to a head of an athlete during an athletic event. A sensor assembly is mounted within one of a mouth guard and a lip guard worn by the athlete and configured to measure at least one of the linear acceleration, angular velocity, angular acceleration, and orientation of the sensor assembly. A data transform component is operatively connected to the sensor assembly and configured to calculate the acceleration of at a center of gravity of the head from the measured at least one of the linear acceleration, angular velocity, angular acceleration, and orientation of the sensor assembly and a position of the sensor assembly relative to the center of gravity of the head. A system interface is configured to provide the calculated acceleration at the center of gravity to one of the athlete, a coach of the athlete, a family member of the athlete, a trainer of the athlete, an official associated with the athletic event, and an audience associated with the athletic event.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

In accordance with an aspect of the present invention, one or more sensor assemblies for detecting and characterizing impacts to a mammalian head are provided. To this end, sensor assemblies can be fixedly attached to the head in one or more locations, and the measurements taken at each location can be used to calculate kinematics and kinetics taking place at any desired location, including a center of gravity, within the head or neck. From this data, it is possible to accurately estimate the effects of a given impact on a user, allowing an observer to act to protect a user in response to an impact, or sequence of impacts, ranging in severity from minor to severe.

Figure 1:
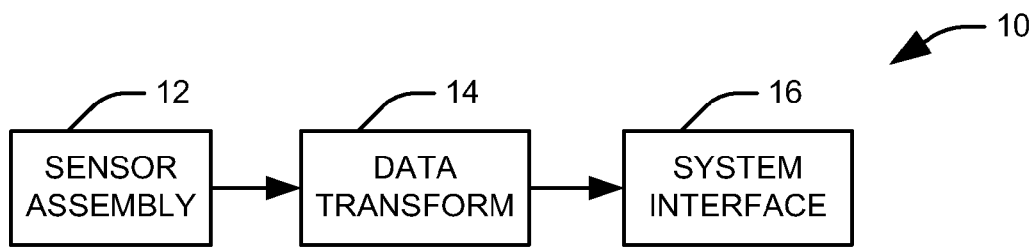
FIG. 1 illustrates an impact monitoring system configured to detect and characterize impacts to a mammalian head.

FIG. 1 illustrates an impact monitoring system 10 configured to detect and characterize impacts to a mammalian head. The term "head" is used generally herein to indicate any portion of the cranium, brain, maxilla, mandible and mouth structures (e.g., teeth), occipito-cervical region, low cervical region (C5, C6, and C7 vertebrae), and associated portions of the spinal cord, as well as any other head and neck structures which could be adversely effected by a directly applied and/or a transmitted impact force (e.g., the head snaps back after a body tackle). The system 10 includes at least one sensor assembly 12 positioned in the vicinity of the head. In accordance with an aspect of the present invention, each sensor assembly 12 is configured to measure at least one of the linear acceleration, angular velocity, angular acceleration, and orientation of the sensor assembly 12 along any desired axis or set of orthogonal axes. In the one implementation, the sensor assembly 12 can include microelectromechanical systems (MEMS) sensors configured to measure one or more of the linear acceleration, angular velocity, angular acceleration and orientation (i.e., angular position) of the head at the point of affixation of the sensor. It will be appreciated that the sensor assembly 12 can be placed in any appropriate apparatus that can be fixedly mounted to, within, or in an otherwise operative relationship to a mammalian head, such as a helmet, mouthpiece, instrument inserted in the auditory canal, mounted in the nasal canal, affixed to the skin, placed in a headband, inserted into eyewear, or any other suitable apparatus.

In one implementation, the sensor assembly 12 can be mounted within a mouthpiece apparatus. Here, a mouthpiece may be a dental/orthodontic appliance (e.g., retainer), mouth guard, lip guard, dental implant (e.g., prosthetic tooth), or any other suitable device located, temporarily or permanently, within a user's oral cavity. In accordance with an aspect of the present invention, it has been determined that the use of a mouthpiece provides several advantages. To begin with, participants in many helmeted (e.g., football, military, hockey, lacrosse, amateur boxing, wrestling, motocross, bicycling) and non-helmeted (basketball, professional boxing and mixed martial arts, soccer, field hockey, rugby, Australian Football, multisport, golf) activities already utilize a protective or vanity mouthpiece, which may facilitate quick acceptance and general usage of the described sensing mouthpiece assembly. Further, a firm coupling between the sensors associated with the mouthpiece apparatus and the head is achieved from tight fitting between the teeth and mouthpiece substrate material and surface tension provided by saliva, and is bolstered by jaw clenching during activity or in response to impending impact. A mouthpiece implementation is thus expected to provide a high degree of kinematic and kinetic calculation accuracy while using a device that is of a format already familiar to, and accepted by, participants in the recreation, military, or other mouthpiece-using activity.

The mouthpiece can be formed from any appropriate material for absorbing shock between the maxilla (upper jaw) and mandible (lower jaw) and/or material designed to induce cervical spine muscle activation in response to impending head impact while having sufficient flexibility to conform to the mouth and contain the sensor assembly 12. The sensor assembly 12 may be encapsulated entirely by surrounding material of the mouthpiece, embedded partially in the material (e.g., a substrate), and/or placed in non-surrounding contact with the material (e.g., attached to a surface of a mouthpiece). In one implementation, the mouthpiece is formed from multiple layers of material, with one layer including sensors mounted, for example, in an elongate pattern. This allows for quick insertion/removal of the sensor assembly 12 and allows worn-out parts to be replaced. The sensor strip can comprise a plurality of MEMS-based linear and rotational kinematic sensors.

In an exemplary implementation, the sensor strip includes six embedded linear accelerometers, three embedded angular velocity sensors and three embedded tilt sensors. It will be appreciated, however, that this sensor configuration is merely given for the purpose of example, and implementations using just an array of linear accelerometers or just an array of angular velocity/angular acceleration sensors are also envisioned. Essentially, any appropriate number and combination of linear accelerometers, angular accelerometers, angular velocity sensors, or orientation sensors can be utilized in accordance with an aspect of the present invention. Example linear accelerometers that can be used are capable of measuring linear acceleration up to two thousand times the standard gravitational acceleration, example angular velocity sensors that can be used are configured to measure angular velocity up to one hundred radians per second, example angular accelerometers that can be used are capable of measuring angular acceleration up to fifty thousand radians per second squared and example orientation sensors that can be used are configured to measured position in space over a full three hundred sixty degree arc, far exceeding typical athlete head impacts of one or two hundred times the standard gravitational acceleration, twenty-five to fifty radians per second, five to ten thousand radians per second squared and orientation of one hundred eighty degrees. Each sensor footprint may occupy a volume of approximately four millimeters by four millimeters by two millimeters. Further, it will be appreciated that, in accordance with an aspect of the present invention because of the generic nature of the algorithm used to calculate localized head kinematics and kinetics, the placement and number of the sensors can be essentially arbitrary, such that no specific relationship among the positions or type of the plurality of sensors is required.

The mouthpiece can further include a component for wireless data transmission to allow the sensor data to be provided to an external processor. For example, the mouthpiece can include a radio frequency (RF) or microwave transmitter operating with an appropriate transmission protocol and a miniature antenna.

To facilitate capture and transfer of the data, the mouthpiece can include a flash memory accessible in a wired or wireless manner. For example, a port can be provided on the mouthpiece to allow data to be transferred to a computer via a universal serial bus (USB) or other connection. The sensors and the transmitter can be powered by an on-board battery, which can be shaped to fit the contour of the mouthpiece. For example, the mouthpiece can include an on-board wired transmitter with data storage. It will be appreciated that the mouthpiece can further include physiochemical sensors to monitor internal body metrics such as, but not limited to, temperature, hydration, pH, glucose level, sodium concentration, oxygen saturation, troponin, and respiration.

In accordance with an aspect of the present invention, the data collected by the sensors can be provided to a data transform component 14 configured to calculate the kinematics and kinetics at a location of interest within the head and neck of an individual wearing the sensor assembly 12. The location of interest can include, any location within the wearer's head or neck including, for example, any of the frontal lobe, parietal lobe, temporal lobe, occipital lobe, cerebellum, medulla oblongata, pons, thalamus, gyrus, fornix, amygdyla, hippocampus, cranium, facial bones, maxilla, mandible, cerebrospinal fluid, occipito-cervical junction, cervical spine, vertebral bodies, spinal cord, spinal nerves, spinal vessels, basal ganglia, peri-vascular spaces, septum, white-gray matter junctions, bridging veins, corpus callosum, fissure, cavity sinus, meninges, falx, dura, arachnoid, and pia matter of the wearer. The location of interest can also include a center of gravity of the wearer's head or head/neck mass.

It will be appreciated that the data transform component 14 can be implemented as dedicated hardware, software executed on a general purpose processor, or some combination of dedicated hardware and software. Further, the data transform component 14 can be implemented on a platform associated with the sensors (e.g., a mouthpiece or helmet), in a processing unit worn by the player either hardwired or wirelessly connected to the sensor assembly, at a remote location, or distributed across multiple discrete processing components. One or more of linear acceleration, angular acceleration, angular velocity, and orientation are measured at the sensor assembly, and data derived from head anthropometry can be used to calculate corresponding linear and angular head kinetics and kinematics at any location on or within the head and neck. For example, the position of each sensor assembly 12 relative to the location of interest can be determined and registered at the data transform component 14.

In one implementation, the location of interest can be represented as a static location during the impact, and translation of the sensor data at the data transform component 14 can be accomplished according to the following "rigid body" relationship between the measured kinematics at a sensor, $\tilde{a}_{mouth}(t)$, $\tilde{\omega}(t)$, $\tilde{\alpha}(t)$ and the acceleration at the location of interest, $\tilde{a}_{LOC}(t)$:

$$\tilde{a}_{LOC}(t)=\tilde{a}_{mouth}(t)+\tilde{\omega}(t)\times(\tilde{\omega}(t)\times\tilde{\rho})+\tilde{\alpha}(t)\times\tilde{\rho} \quad \text{Eq. 1}$$

where $\tilde{\omega}(t)$ is the measured or calculated angular velocity of the head, $\tilde{\alpha}(t)$ is the measured or calculated angular acceleration of the head and $\tilde{\rho}$ is a displacement between the sensor and the location of interest determined from the head anthropometry.

In accordance with an aspect of the present invention, the position of each sensor assembly relative to the location of interest can be represented as a time-varying function. By a "time-varying function," it is meant that the spatial relationship defined by the function can vary over the time period of a given impact. For example, in any significant impact, the brain will move around in the skull, such that the position of tissue located at the location of interest relative to any external landmarks on the head varies for a period of time after the impact. Accordingly, the relative location can be expressed as a function of the kinematic values measured at the sensors as well as the measured head anthropometry. In accordance with an aspect of the present invention, the data transform component 14 can incorporate a model of the movement of the brain, given a set of anthropometric parameters describing the head, when exposed to various kinematics and kinetics, including linear acceleration, angular acceleration, angular velocity, orientation change, impact force, and energy absorption among others. For example, the location of interest can be represented as a plurality of time-varying functions, with a given function selected according to the kinematic values measured at the sensor assembly 12. By tracking the movement of the location of interest induced by the impact, the linear acceleration, angular acceleration, angular velocity, and orientation changes experienced there, and the corresponding physiological effects, can be calculated more accurately via this "deformable body" approach.

In this implementation, translation of the sensor data at the data transform component 14 can be accomplished according to the following relationship between the acceleration at a sensor, $\tilde{a}_{mouth}(t)$, and the acceleration at the location of interest $\tilde{a}_{INT}(t)$:

$$\tilde{a}_{INT}(t)=\tilde{a}_{mouth}(t)+\tilde{\omega}(t)\times(\tilde{\omega}(t)\times\tilde{\rho}(t))+\tilde{\alpha}(t)\times\tilde{\rho}(t)+\ddot{\tilde{\rho}}_r(t)+2\tilde{\omega}(t)\times\dot{\tilde{\rho}}_r(t) \quad \text{Eq. 2}$$

where $\tilde{\omega}(t)$ is the measured or calculated angular velocity of the head, $\tilde{\alpha}(t)$ is the measured or calculated angular acceleration of the head, $\tilde{\rho}(t)$, $\dot{\tilde{\rho}}_r(t)$ and $\ddot{\tilde{\rho}}_r(t)$ are functions representing time-varying displacement, velocity and acceleration, respectively between the sensor and the location of interest of the head and determined from the head anthropometry and the kinematic data measured at the sensors.

The calculated kinematics and kinetics at the location of interest, including acceleration, is provided to a system interface 16, where the information is provided to an observer in a human-comprehensible form. For example, the kinematic and kinetic values associated with a head impact and the various measured physiological parameters of a user in real time can be shown to an observer at an associated display. The measured data can, for instance, be used to score a boxing or MMA competition or provide supplementary content to enrich the fan experience in person or remotely.

To enhance the safety of these events or other events likely to produce significant impacts to the head and neck, the measured and calculated kinematic and kinetic data can be displayed to an observer and/or trigger a remote warning device(s) when a user exceeds a critical head impact or physiological threshold. For example, the system interface 16 can include an on-board warning device that alerts the observer when the calculated acceleration exceeds a threshold value. Where desired, the sensor data can be used to activate an associated intervention system, human or automated, to prevent injury to the user. The system interface 16 can also provide quantitative measures for correlation with post-event neurological assessment, including physical exams, blood exams, genetic typing, and imaging modalities such as coherence tomography, magnetic resonance imaging, diffusion tensor imaging, and positron emission tomography, and the like. It is believed that an individual's susceptibility to many neurocognitive disorders later in life can be enhanced even by repeated minor impacts to the head. Accordingly, the system interface 16 can be configured to tabulate head impact cumulatively, such as during training or over the course of an athlete's career or portion thereof, as an aid to diagnosis, study, or prevention of long-term neurocognitive disorders, including Parkinson's disease, loss of memory, dementia pugilistica, second impact syndrome, psychiatric disorders, and Alzheimer's disease.

Figure 2:
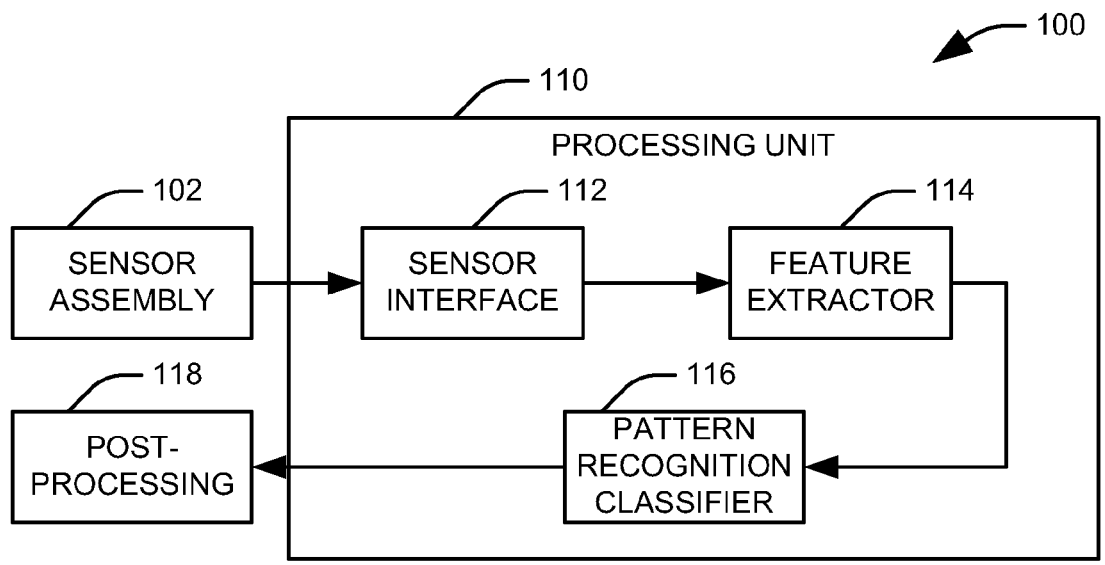
FIG. 2 illustrates a classification system for classifying an impact into an associated event class in accordance with an aspect of the present invention.

FIG. 2 illustrates a classification system 100 in accordance with an aspect of the present invention. The classification system 100 comprises at least one sensor assembly 102 deployed as to be substantially fixedly engaged with a human head. In the illustrated implementation, the sensor assembly 102 is engaged with the head of a participant in an athletic event, for example, as part of a mouthpiece or on a surface of a helmet, though any suitable substantially fixed engagement may be used. For example, the sensor assembly 102 could also or instead be located in a replacement tooth implant, an auditory canal implant, a helmet liner, headband, eyewear, stuck to the skin surface, inserted into the nasal cavity, or even as a direct attachment to the head via a skull anchor or the like. The sensor assembly 102 is operative to measure the kinematics of the head along any desired axis, including three mutually orthogonal axes, at the location of the sensor as well as measuring the angular acceleration, angular velocity, and orientation of the head about any coincident or non-coincident axis or set of axes.

In accordance with an aspect of the present invention, the classification system 100 is configured to measure the kinematics induced by an impact to the head monitored by the sensor assembly 102 and categorize the impact as one of a plurality of event classes via calculated kinematics and kinetics at any desired location on the head. In one implementation, the various event classes can correspond to ranges of likelihood for various head and neck injuries given the measured impact, such as traumatic brain injuries, concussions, sub-concussion injuries, facial fractures, skull fractures, jaw fractures, and spinal cord injuries. It will be appreciated that training data for a classifier system can be initially derived from cadaver studies, animal studies, and/or computer or mechanical simulations and refined with data collected during usage of the device. For example, a first set of classes could represent ranges of probabilities of a concussion or sub-concussion injury given the measured impact, a second set of classes could represent ranges of probabilities of a skull fracture given the measured impact, and a third set of classes could represent ranges of probabilities of neck injury given the measured impact. From the determined class, an observer, such as a coach or trainer, can make decisions about a user's, such as an athlete's, further participation in an event or the desirability of additional protective and/or diagnostic measures. Further, the determined event class can provide an instantaneous on-site or off-site triage tool for a physician in diagnosing and treating a potential injury to the head or neck arising from the measured impact.

In another implementation, the various event classes can represent an origin or associated type of the impact. For example, where the athletic event is a boxing match, the various event classes could represent a hook, an oblique hook, a jab to the forehead or face, an uppercut, a cross, or an overhand punch. The classes could be further refined to identify the type and handedness of a punch or other strike (e.g., left or right). In an MMA match, the classes could be further expanded to include various kicks as well as the impact of elbows and knees to the head. For American football, the type and severity of contact, for example, helmet-to-helmet, helmet-to-shoulder, helmet-to-foot, helmet-to-object, helmet-to-elbow, helmet-to-knee, and/or helmet-to-ground—can be ascertained. And for soccer, head-to-head contacts can be delineated from head-to-elbow or head-to-goalpost impacts. For various contact sports, the classes can represent the type and severity of an impact between two players, such that the plurality of impact classes can include a bare head-to-bare head contact class, a bare head-to-knee class, a bare head-to-elbow class, a bare head-to-foot class, a bare head-to-shoulder class, bare head-to-object class, bare head-to-body class and a bare head-to-ground class.

Such information could be utilized for scoring purposes, possibly by being provided to a graphical user interface for a recorded or computer generated "instant replay" of the action as well as for summarizing the action of a match for later review. Further, in accordance with an aspect of the present invention, the event class information can be used to provide a computer simulation of the match, for example, to enhance the viewing experience for spectators or to drive advanced brain injury finite element models.

To this end, the sensor data is provided to a processing component 110 configured to provide a human-comprehensible output from the sensor data. A sensor interface 112 is configured to determine kinematics and kinetics, including a linear acceleration, at a location of interest, such as the center of gravity of the head, from the sensor data. It will be appreciated that the transform of the kinematics data from the sensor to provide kinematic and kinetic data at the location of interest can be performed either by assuming a static tissue location—"rigid body"—or with a dynamic tissue location represented by a time-varying function—"deformable body".

The transformed sensor data is then provided to a feature extractor 114 that extracts a plurality of features from the transformed data. In accordance with an aspect of the present invention, the plurality of features can be selected to include at least one feature that is a function of the kinematics and/or kinetics of the head at the location of interest.

One set of parameters that are useful as classification features can be derived as functions of the linear acceleration at the location of interest. For example, a magnitude of the acceleration at the location of interest can be determined from the acceleration along each of the three coordinate axes, and a resultant jerk at the location of interest can be calculated as the time derivative of the magnitude of the acceleration. Similarly, a direction of the acceleration can be determined from the acceleration along each axis. The change in the velocity of the head in a given direction, or delta-V, can be determined by integrating the determined acceleration of the location of interest along that direction, and a corresponding linear momentum can be determined as the product of the change in velocity and a mass of the head. For example, the mass of the head can be estimated from head anthropometry. Similarly, a kinetic energy of the head can be determined as one-half the product of the mass of the head and the square of the change in velocity, and a power imparted to the head can be determined as the time derivative of the kinetic energy. The metrics can also include any of a peak pressure, a strain, a strain rate, a product of the strain and strain rate, a von Mises stress, a strain energy, and a sheer stress. Each of these metrics can be represented as a time series, with multiple values for each metric each representing associated times during the impact.

Several additional metrics can be derived from the measured and calculated linear acceleration values when the location of interest is a center of gravity of the head, such as an impact force along each axis, calculated as the product of the mass of the head and the acceleration at the center of gravity along each axis, and a magnitude of the impact force. A loading rate can be determined as the time derivative of the impact force, and minimum and maximum values of this loading rate can be utilized as features. A duration of the impact can be calculated based on the length of the loading and unloading pulse after initial contact as based on impact force.

A value representing the Gadd Severity Index (GSI) can be calculated as:

$$GSI = \int_0^T \tilde{a}_R(t)^{2.5} \, dt \qquad \text{Eq. 3}$$

where $\tilde{a}_R(t)$ is the resultant magnitude of the calculated linear acceleration at the center of gravity expressed as a multiple of the standard gravitational acceleration at Earth's surface (g=9.81 m/s$^2$), and the period [0:T] is an essential impact duration. In one implementation, this duration is selected to be fifteen milliseconds.

A value for the Head Injury Criterion (HIC) can be calculated as:

$$HIC = (t_2 - t_1)\left[\frac{1}{t_2 - t_1} \int_{t_1}^{t_2} \tilde{a}_R(t) \, dt\right]^{2.5} \qquad \text{Eq. 4}$$

where $\tilde{a}_R(t)$ is the resultant magnitude of the calculated linear acceleration at the center of gravity expressed as a multiple of the standard gravitational acceleration and the period $[t_1:t_2]$ is a time period for which the HIC is maximized, referred to as the HIC duration. In one implementation, the HIC duration, equal to $t_2-t_1$, can also be utilized as a classification feature.

A Skull Fracture Correlate (SFC) value can be calculated as:

$$SFC = \left[\frac{\max(\text{Delta} - V_R(t))}{HIC \text{ Duration}}\right]\frac{1}{g} \quad \text{Eq. 5}$$

where g is standard gravitational acceleration and Delta-$V_R(t)$ is the resultant change in velocity of the head.

A second set of parameters useful for event classification are derived as functions of the angular velocity and angular acceleration of the head. For example, a magnitude of the angular acceleration can be determined from the acceleration about each of the three coordinate axes, and a magnitude of the angular velocity can be determined from the velocity about each of the three coordinate axes. A jerk resulting from the angular acceleration can be calculated as the time derivative of the magnitude of the angular acceleration. A head angular momentum can be determined from the angular velocity about each axis and a corresponding moment of inertia. The moments of inertia can be estimated from the head anthropometry. A magnitude of the angular momentum can be determined from the angular momentum about each of the three coordinate axes. Each of these metrics can also be represented as a time series, with multiple values for each metric each representing associated times during the impact.

A Generalized Acceleration Model for Brain Injury Threshold (GAMBIT) can be calculated as:

$$GAMBIT(t) = \left[\left(\frac{\tilde{a}_R(t)}{\tilde{a}_C}\right)^{2.5} + \left(\frac{\tilde{a}_R(t)}{\tilde{a}_C}\right)^{2.5}\right]^{\frac{1}{2.5}} \quad \text{Eq. 6}$$

where $\tilde{a}_R(t)$ is the resultant magnitude of the linear acceleration at the center of gravity expressed as a multiple of the standard gravitational acceleration, $\tilde{a}_C$ is a critical linear acceleration equal to two hundred fifty times the standard gravitation acceleration, $\alpha_R(t)$ is a resultant magnitude of the angular acceleration, and $\alpha_C$ is a critical angular acceleration equal to twenty-five thousand radians per second.

A Weighted Principal Component Score (wPCS) can be calculated as:

$$wPCS = \quad \text{Eq. 7}$$

$$k_{lat} \times 10 \left(\left[\begin{array}{c} k_{GSI}\left(\frac{GSI - GSI_m}{GSI_{sd}}\right) + k_{HIC}\left(\frac{HIC - HIC_m}{HIC_{sd}}\right) + \\ k_{LIN}\left(\frac{\max(\tilde{a}_R(t)) - a_m}{a_{sd}}\right) + k_{ROT}\left(\frac{\max(\tilde{\alpha}_R(t)) - \alpha_m}{\alpha_{sd}}\right) \end{array}\right] + 2\right)$$

where is $k_{lat}$ is a weight with a value of 1 for a lateral impact, $k_{GSI}$ is a weight with a value of 0.4718, $k_{HIC}$ is a weight with a value of 0.4720, $k_{LIN}$ is a weight with a value of 0.4336, $k_{ROT}$ is a weight with a value of 0.2164, $HIC_m$ is a mean value of the HIC over a plurality of sample impacts, $HIC_{sd}$ is a standard deviation of the HIC over the plurality of sample impacts, $GSI_m$ is a mean value of the GSI, $GSI_{sd}$ is a standard deviation of the GSI, $a_m$ is a mean value of the linear acceleration at the center of gravity, $a_{sd}$ is a standard deviation of the linear acceleration at the center of gravity.

A Head Impact Power (HIP) can be calculated as:

$$HIP = m_{head}[\tilde{a}_{CGX}(t)\int\tilde{a}_{CGX}(t)dt + \tilde{a}_{CGY}(t)\int\tilde{a}_{CGY}(t)dt + \tilde{a}_{CGZ}(t)\int\tilde{a}_{CGZ}(t)dt] + +I_X\tilde{\alpha}_X(t)\int\tilde{\alpha}_X(t) + I_Y\tilde{\alpha}_Y(t)\int\tilde{\alpha}_Y(t) + I_Z\tilde{\alpha}_Z(t)\int\tilde{\alpha}_Z(t) \quad \text{Eq. 8}$$

where $m_{head}$ is a mass of the head, determined from anthropometric data, $\tilde{a}_{CGX}$ is an acceleration at the center of gravity along a anterior-posterior axis, $\tilde{a}_{CGY}$ is an acceleration at the center of gravity along a lateral axis, $\tilde{a}_{CGZ}$ is an acceleration at the center of gravity along an cranio-caudal axis, $\alpha_X$ is an angular acceleration about a anterior-posterior axis, $\alpha_Y$ is an angular acceleration about a lateral axis, $\alpha_Z$ is an angular acceleration about an cranio-caudal axis, $I_X$ is a head mass moment of inertia about a anterior-posterior axis, $I_Y$ is a head mass moment of inertia about a lateral axis, and $I_Z$ is a head mass moment of inertia about an cranio-caudal axis.

A number of additional features can be determined by modeling the measured impact in a finite element model of the brain. For example, features can be generated corresponding to percentages of the volume of the brain experiencing various levels of principal strain. In the illustrated implementation, each of a first percentage of the brain volume experiencing a principal strain exceeding five percent, a second percentage of the brain volume experiencing a principal strain exceeding ten percent, and a third percentage of the brain volume experiencing a principal strain exceeding fifteen percent can be used as features. Similarly, a dilation damage measure (DDM) can be calculated from the model as a percentage of brain volume experiencing a negative pressure less than 101.4 kilopascals. A relative motion damage measure (RMDM) can be calculated as:

$$RMDM = \frac{\varepsilon(t)}{\varepsilon_F(t, \dot{\varepsilon}(t))} \quad \text{Eq. 9}$$

where $\epsilon(t)$ is a bridging vein strain, as determined by the finite element model, and $\epsilon_F(t, \dot{\epsilon}(t))$ is a strain associated with bridging vein failure at a given strain rate, as determined by the finite element model.

Similarly, a possibility of neck injuries can be accessed via a calculated force at the occipital-cervical junction along each axis and a determined occipital moment about each axis, as well as a magnitude of the force and the occipital moment. A Neck Injury Criterion ($N_{ij}$) can be calculated as:

$$N_{ij} = \max\left[\frac{\tilde{F}_{occZ}(t)}{F_{Zcrit}} + \left(\frac{\tilde{F}_{occY}(t) * d + \tilde{M}_{occX}}{M_{Xcrit}}\right)\right] \quad \text{Eq. 10}$$

where $\tilde{F}_{occZ}(t)$ is the occipital force along an cranio-caudal axis, $\tilde{F}_{occY}(t)$ is the occipital force along a lateral axis, $\tilde{M}_{occX}$ is the occipital moment about a anterior-posterior axis, $F_{Zcrit}$ is a critical occipital axial force equal to 6806 Newtons, $M_{Xcrit}$ is a critical occipital moment equal to one hundred thirty-five Newton-meters, and d is a distance equal to 0.01778 meters.

The calculated features are then provided to a pattern recognition classifier that selects an event class representing the impact from a plurality of event classes. The pattern recognition classifier 116 can utilize any of a number of classification techniques to select an appropriate event class from the plurality of numerical features. Further, the pattern recognition classifier 116 can utilize features that are not derived from the sensor data, such as an age, height, or weight of the user and one or more numerical parameters derived from a medical history of the user, such as a recorded history of previous sensed head impacts. In one implementation, the pattern recognition classifier 116 comprises a rule based classifier that determines an event class according to a set of logical rules. Alternatively, the pattern recognition classifier 116 can comprise a Support Vector Machine (SVM) algorithm or an artificial neural network (ANN) learning algorithm to determine an occupant class for the candidate occupant. A SVM classifier can utilize a plurality of functions, referred to as hyperplanes, to conceptually divide boundaries in an N-dimensional feature space, where each of the N dimensions represents one feature (e.g., layer characteristic) provided to the SVM classifier. The boundaries define a range of feature values associated with each class. Accordingly, an output class can be determined for a given input according to its position in feature space relative to the boundaries.

An ANN classifier comprises a plurality of nodes having a plurality of interconnections. The layer characteristic values are provided to a plurality of input nodes. The input nodes each provide these input values to layers of one or more intermediate nodes. A given intermediate node receives one or more values from previous nodes. The received values are weighted according to a series of weights established during the training of the classifier. An intermediate node translates its received values into a single output according to a transfer function at the node. For example, the intermediate node can sum the received values and subject the sum to a binary step function. These outputs can in turn be provided to addition intermediate layers, until an output layer is reached. The output layer comprises a plurality of outputs, representing the output classes of the system. The output class having the best value (e.g., largest, smallest, or closest to a target value) is selected as the output class for the system.

The selected event class is provided to a post-processing component 118 configured to provide the event class to a human operator in a human-comprehensible form. For example, the human operator can include one or more of an athlete, a coach of the athlete, a family member of the athlete, a trainer of the athlete, an official associated with an athletic event, and an audience associated with the athletic event. The post-processing component 118 can include a display that simply displays a label associated with the class, a computer simulation or animation, or even a simple auditory or visual indicator that alerts an observer than a user may have sustained an impact that falls within the selected event class. In one implementation, the post-processing component 118 includes a graphical user interface to allow a user, such as an audience member, to customize the presentation of the event class or other data derived from the sensor assembly 102. For example, the graphical user interface could be configured to allow a user to define a condition related to the representation of the determined acceleration and place a wager contingent on a future occurrence of the defined condition.

In view of the foregoing structural and functional features described above, a methodology in accordance with various aspects of the present invention will be better appreciated with reference to FIGS. 3-8. While, for purposes of simplicity of explanation, the methodologies of FIGS. 3-8 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention.

Figure 3:
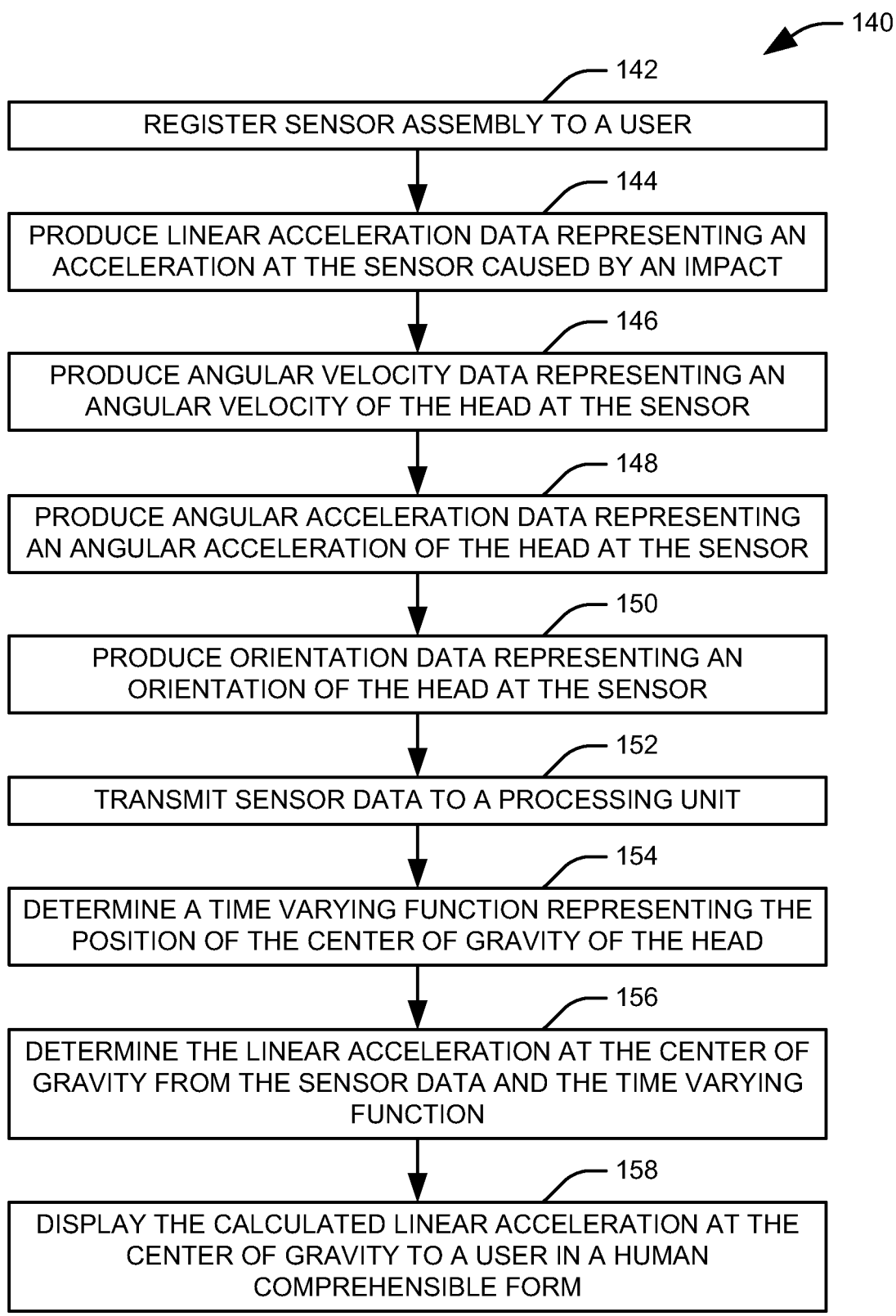
FIG. 3 illustrates one example of a method for determining kinematics and kinetics at a center of gravity of a user's head in accordance with an aspect of the present invention.

FIG. 3 illustrates one example of a method 140 for determining one of kinematics and kinetics at an arbitrary location of the head in accordance with an aspect of the present invention. For the purpose of example, this method describes determining kinematics and kinetics at a center of gravity of a user's head, as it has been determined, in accordance with an aspect of the present invention, kinematic and kinetic data at the center of gravity is a useful predictor in classifying head impact events. The method begins at 142, where a sensor assembly is initialized for use for a given user and attached to the user's head in a substantially rigid manner to an ambient-accessible surface of the user's head (e.g., in a mouthpiece or an implant within the auditory canal). For example, various measurements of the user's head can be taken and one or more values or time varying functions representing a center of gravity of the head of that user can be determined. In one implementation, a position and orientation of the sensor within the mouthpiece as it is worn by a user can be determined via lateral and anteroposterior x-rays to directly register the location of the sensors relative to a center of gravity.

At 144, linear acceleration data is produced from the sensor assembly representing acceleration experienced by the user's head at the site of the at least one sensing device. In one implementation, the sensor assembly is configured to be responsive only to impacts producing a predetermined acceleration, such that impacts below a threshold acceleration are not stored or transmitted. The sensor assembly can be configured to conserve power in a sleep mode, with the sensors only powered fully when collecting data in bursts. It will be appreciated that the sensor assembly can include one or more signal conditioning elements configured to take raw voltage data from sensors and convert to an appropriate signal for storage/transmission. For example, the signal conditioning elements can include one or more amplifiers, integrators, filters, and multiplexers for providing a coherent signal for one or both of transmission and storage. At 146, angular velocity data indicative of an angular velocity of the user's head is provided by the sensor assembly. At 148, angular acceleration data indicative of an angular acceleration of the user's head is provided by the sensor assembly. At 150, orientation data indicative of an orientation of the user's head is provided by the sensor assembly.

At 152, the sensor data is transmitted to a processing component, for example, via a wired or RF wireless connection. At 154, a location of the center of gravity of the user's head relative to a position of the at least one sensing device is determined as a function of time from the registered location data and the sensor data. For example, the processing unit can comprise a look-up table containing various time varying functions representing the position of the center of gravity, and a given function can be selected according to associated ranges of linear acceleration, angular velocity, angular acceleration, and orientation data measured.

At 156, the acceleration at the center of gravity of the user's head is calculated as a function of the sensor data, the represented location of the center of gravity of the user's head, the angular velocity data, the angular acceleration data, and the orientation data. At 158, the calculated kinematic and kinetic data are then provided to at least one of the user and an observer in a human-perceptible form. For example, the mouthpiece could be configured to provide an auditory, visual, and/or tactile stimulus to the user and/or an observer in response to an impact producing a dangerous level of acceleration. Alternatively, the calculated kinematic and kinetic data can be provided to an observer at an associated display.

Figure 4:
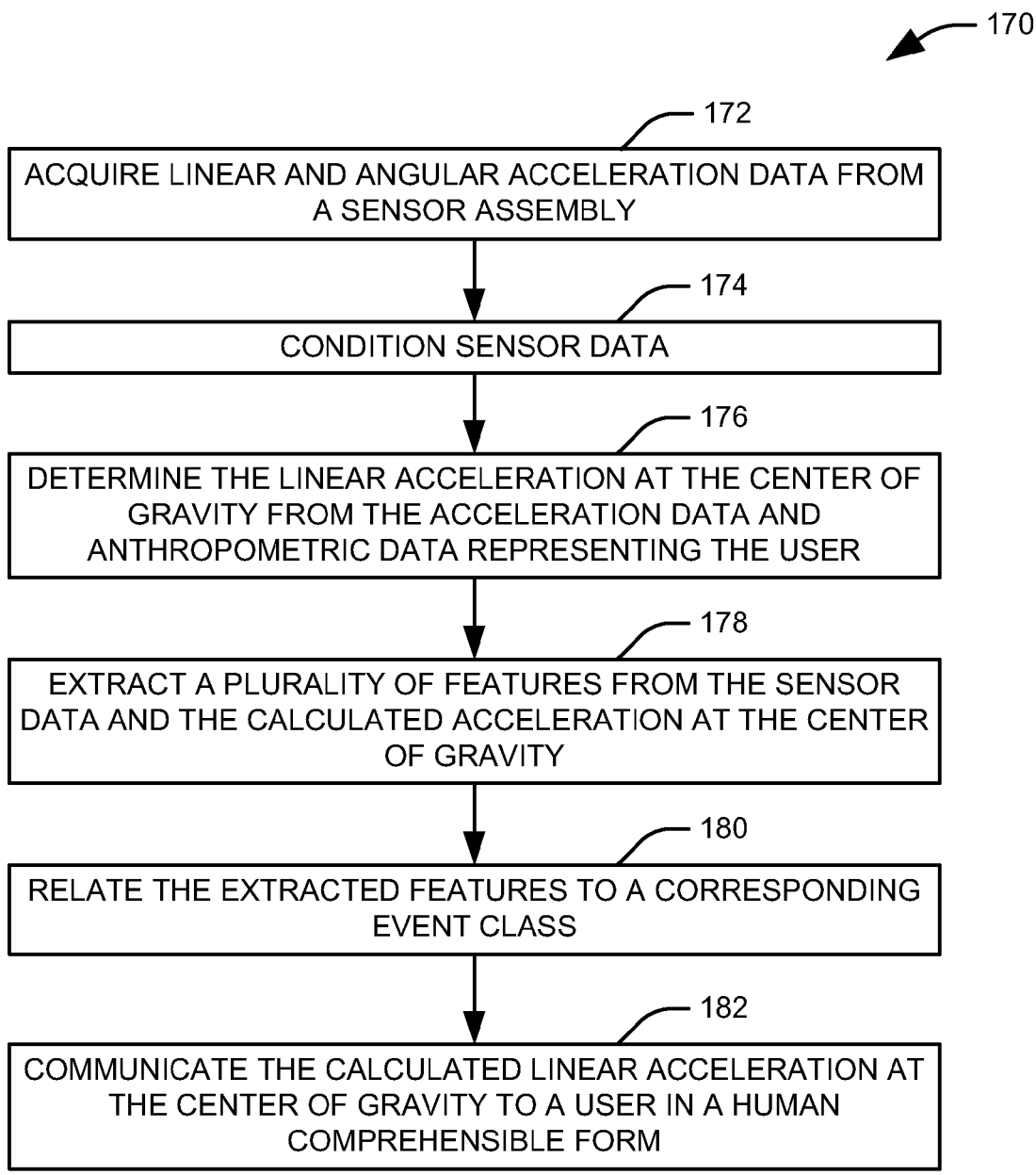
FIG. 4 illustrates one example of a method for classifying an impact into an event class in accordance with an aspect of the present invention.

FIG. 4 illustrates a methodology 170 for classifying an impact into an event class in accordance with an aspect of the present invention. At 172, at least one of linear acceleration data, angular velocity data, angular acceleration data, and orientation data are acquired from a sensor assembly. For example, the sensor assembly can include one or more of a plurality of linear accelerometers, a plurality of angular velocity sensors, and a plurality of orientation sensors, and the angular acceleration can be determined from the angular velocity. At 174, the sensor data is conditioned to enhance the raw sensor data, eliminate obvious noise, and otherwise prepare the sensor data for further processing. At 176, the conditioned sensor data and known anthropometric parameters of a user are used to calculate the linear and rotational kinematics and kinetics at the center of gravity of the head.

At 178, a plurality of features are extracted from the sensor data. In accordance with an aspect of the present invention, a subset of at least two of the plurality of features can be derived from the calculated kinematics and kinetics at the center of gravity of the head. In addition, the plurality of features can include an age, height, or weight of the user as well as one or more numerical parameters derived from a medical history of the user. The extracted features represent the circumstances of the impact as a vector of numerical measurements, referred to as a feature vector. At 180, the feature vector is related to a most likely event class, based on an appropriate classification technique. For example, the feature vector can be classified via a series of logical rules at an appropriate rule-based expert system. Alternatively, the classification can be performed by a statistical or neural network classifier. In one implementation, the classification technique further provides a confidence value representing the likelihood that the pattern is a member of the selected event class. The confidence value provides an external ability to assess the correctness of the classification. For example, a classifier output may have a value between zero and one, with one representing a maximum certainty.

At 182, the selected event class is conveyed to the user or an observer in a human-comprehensible form. For example, a label associated with the class can be displayed, a computer simulation can be generated to represent the selected event, or an auditory or visual indicator can alert an observer, such as a coach or trainer, when an event class representing a likelihood of a specific neck or head injury that is above a predetermined threshold is selected. Where a confidence value is generated, it can also be provided to the observer to aid in decisions as to the user's further participation in the event or to aid in any medical diagnosis.

Figure 5:
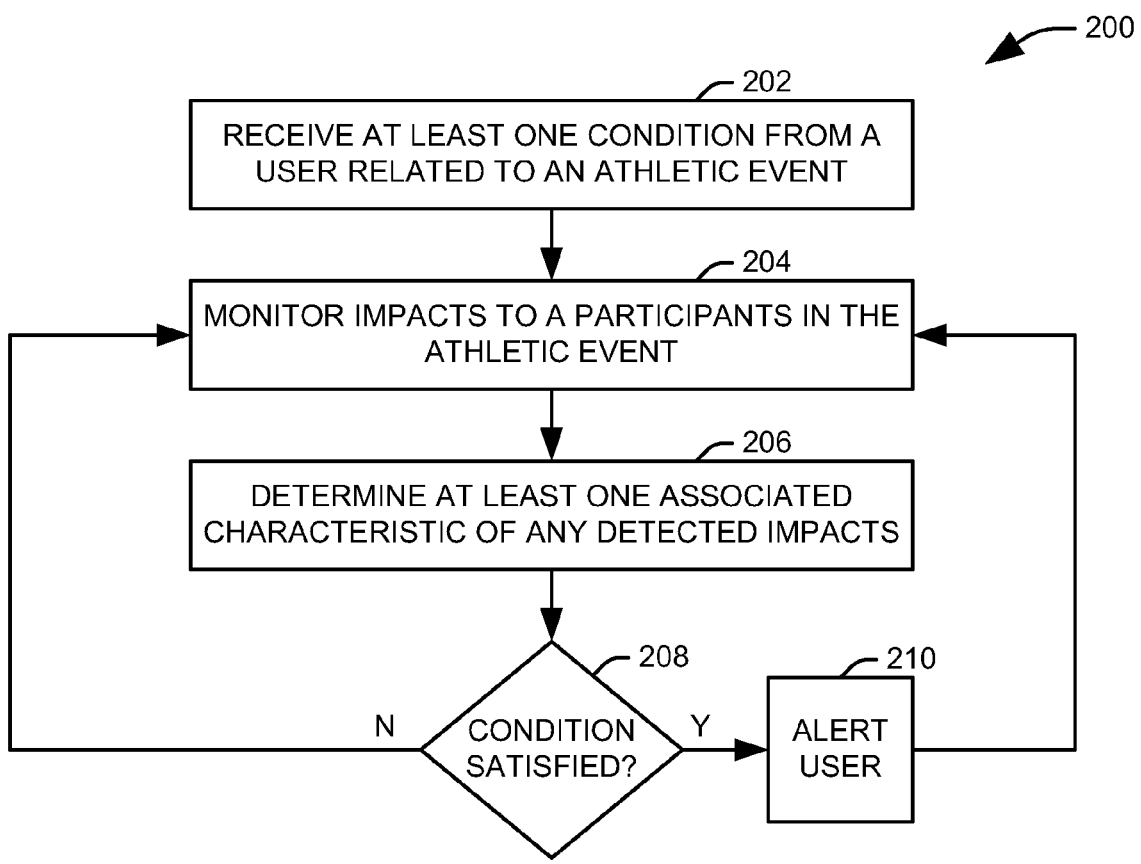
FIG. 5 illustrates a methodology for utilizing an impact monitoring system in accordance with an aspect of the present invention to augment the experience of a non-participant of an athletic event.

FIG. 5 illustrates a methodology 200 for utilizing an impact monitoring system in accordance with an aspect of the present invention to augment the experience of a non-participant of an athletic event. At 202, at least one condition, related to the athletic event, is provided by a non-participating user and received at the impact monitoring system. For example, the at least one condition can be provided to an system interface of the impact monitoring system, such that the various impacts received or delivered by individuals outfitted with the sensor assembly described previously can be compared to the defined conditions.

It will be appreciated that the at least one condition can vary with the desired application. For example, a condition can relate to an impact received by a specific participant, such as an impact having a linear acceleration at the center of gravity of the head greater than a threshold value occurring to a specified participant or an impact that falls within a particular event class (e.g., a helmet-to-helmet impact in American football). The condition could be as simple as the occurrence of any significant impact to a participant's head. It will be appreciated that the condition does not need to be specific to a particular impact, and could represent, for example, a threshold for a cumulative force or acceleration experienced by a given participant. Alternatively, a condition can include the detection of a specific event class, such as a particular impact source. For example, in a boxing match, the condition can be the occurrence of a particular kind of punch or a punch producing a force or imposed acceleration above a threshold value.

At 204, impacts to participants in the athletic event are monitored. At 206, at least one characteristic is determined for any detected impacts. The determined characteristic can include a magnitude of a given impact, an associated location of the impact, or an event class of the impact, such as an impact source, a "legal/illegal" hit determination, or a likelihood of injury represented by the impact. At 208, it is determined if any of the defined conditions are satisfied by the determined characteristic. If not (N), the methodology 200 returns to 202 to continue monitoring for impacts. If so (Y), a user is alerted that the condition has been satisfied at 210, and the methodology 200 returns to 202 to continue monitoring for impacts.

It will be appreciated that the method of FIG. 5 can be used for any of a number of purposes. In one example, the non-participant can be a parent, coach, official, or other person with a direct interest in the well-being of a participant, and the condition can be any impact to the head of the participant or any impact to the participant's head above a threshold level of force or acceleration.

As athletes are becoming faster and regulations are becoming more complex, it has become increasingly difficult for referees to correctly enforce rules of play. This difficult task is made harder by accusations of bias in enforcing these rules. Currently, the majority of rules are enforced based on the subjective observations of the referees. To provide officials with an objective source of data to aid in rule implementation, the condition can be defined as the receipt or initiation of various types of impacts. This information could be used to provide objective scoring for various sports (e.g., boxing and MMA), or rules verification in others (e.g., detecting illegal contact to the head in American football).

The method can also be used for directly entertaining a non-participant. For example, the conditions can represent wagers placed by observers, with the determined characteristics representing a cumulative scoring total, via number or magnitude of impacts imposed or received within a region of interest. It will be appreciated that the conditions can be defined such that only impacts above a threshold magnitude are included in the scoring. Alternatively, the conditions could represent scoring categories in a fantasy sports game, for example, for boxing, American football, or MMA, with the characteristics representing various impact sources (e.g., uppercut, jab, kick, etc.), impact thresholds, and cumulative received or imposed impact totals.

Finally, an ancillary benefit of the collection of impact statistics is the ability to share the accumulated statistics with observers, both local and remote. An observer's benefit from watching the event can be enhanced by the ability to identify the forces the player is receiving during the event. This would be even more useful to an observer with a particular interest in an individual athlete, such as a parent watching their child play high school football or an individual watching a favorite boxer during a match. The impact monitoring system can include the ability to graphically display force of impact both instantaneously and cumulatively. Similarly, a number and type of impacts exceeding a threshold force or acceleration can be displayed to the observers, along with any relevant information from any scoring performed by the system.

Finally, where the system identifies the impact source and location, a computer-generated simulation of the impact can be displayed to the observer.

Figure 6:
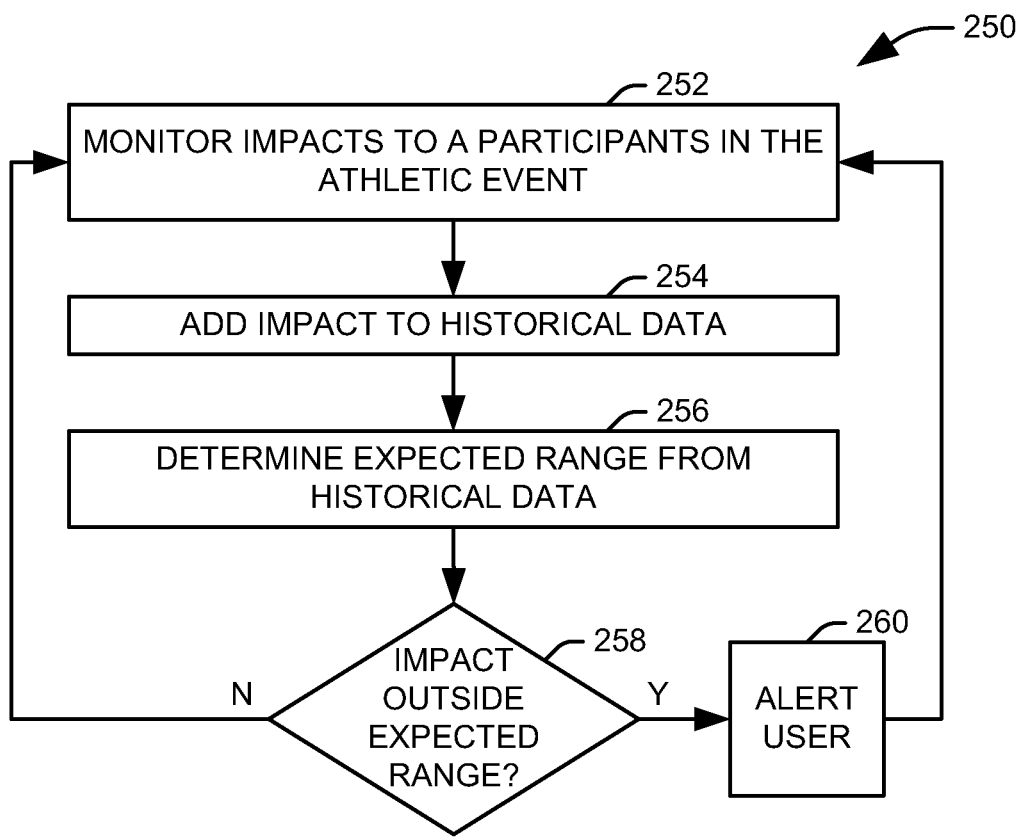
FIG. 6 illustrates a methodology for utilizing an impact monitoring system in accordance with an aspect of the present invention to monitor the performance and condition of an athlete in an athletic event.

FIG. 6 illustrates a methodology 250 for utilizing an impact monitoring system in accordance with an aspect of the present invention to monitor the performance and condition of an athlete in an athletic event. As technology has advanced, so have training methods for sports. In the past, it was acceptable to train based solely on non-biometric information such as distance or time of a run. It has been shown, however, that by modulating the intensity of a workout, better results can be achieved, often in a shorter time. The impact monitoring system can be a powerful aid in measuring the intensity and effectiveness of various training programs, and they can be adjusted for optimal performance improvement based on the data obtained.

One example of this would be strength training for the neck. It has long been thought that emphasizing neck strengthening could improve outcomes in athletes that receive repeated blows to the head by increasing the shock absorbing capability of the neck via its musculature. Likewise, football players that are prone to transient brachial plexus injuries, (commonly termed stingers/burners, or more severe injuries such as transient quadraparesis are often advised that intensive off-season neck strengthening would decrease the incidence of further injuries. The impact monitoring system could objectify the results of such training by capturing the amount of force received before and after training. Since the impact monitoring system can collect these measurements cumulatively, the results could be more effectively interpreted that a system that just measures peak impacts. For example, for training purposes, it would likely be more useful to know that an athlete has thirty percent less force acquired throughout a game than knowing the results of any one impact. Similarly, information received by the impact monitoring system could be used to determine if a competitor is becoming less effective as the competition progresses. For example, in a boxing match, if the amount of force the opponent is receiving from a particular type of punch is declining, it could be interpreted by the observer that the athlete of interest is tiring or has a potential injury. For example, the boxer could be fatigued or have a hand injury.

Improving the athletes' technique can also prevent these injuries. To this end, the impact monitoring system data can be used to determine the effectiveness of the player's retraining in appropriate technique. Many of the newer techniques in sports are designed to minimize trauma to the head. Since these should result in decreased cumulative force registered by the impact monitoring system, it can be used to assess the effectiveness of their learning. For example, an American football player can be trained to avoid leading with the head during a tackle. Conversely, other techniques to increase the force applied to an opponent are practiced in various sports. The effectiveness of these techniques may be assessed by the impact monitoring system data from the opponent. For example, a boxer may work to improve the technique of a punch to increase force, and measure his or her progress by the increase in the force of impacts imposed on opponents. This could be made more powerful if coupled with real time video that is today available in most competitive events.

At 252, impacts to participants in the athletic event are monitored. At 254, the force or acceleration of the measured impact is added to a library of historical data. It will be appreciated that the historical data can represent data captured over the duration of a given athletic event or training session, over the course of all or part of a season or year, or over multiple years, depending on the desired application. The historical data can be represented by a variety of descriptive statistics, including one or more of the mean, median, variance, standard deviation, interquartile range, slope and y-intercept of the impact magnitude against time, and any other appropriate statistics. In general, the historical data will be specific to a given athlete, and only impacts associated with that athlete will be stored. It will be appreciated, however, that an impact monitoring system can store multiple libraries of historical data associated with various athletes of interest.

At 256, an expected range for impacts associated with a given athlete is determined from the historical data. For example, the expected range can be set around an average (e.g., mean or median) performance of the athlete over a given time period during or preceding an event or practice, and the range can be set around the average or another value derived from the average (e.g., the average plus or minus a desired offset value representing improvement) according to an appropriate deviation measure (e.g., standard deviation or interquartile range). Alternatively, the range can be set according to a trend line established from the historical data, to represent a continuation of observed improvement. At 258, it is determined if a given impact or averaged series of impacts delivered or received by the athlete of interest fall within the established range. If the measured impact or average is within the defined range (N), the methodology 250 returns to 252 to continue monitoring impacts. If the measured impact or average falls outside of the defined range (Y), a user, such as a coach or trainer, is alerted at 260, and the methodology 250 returns to 252 to continue monitoring the athlete's status.

In one implementation, multiple impact parameters can be calculated from a determined force or acceleration, and historical data for each impact parameter can be tracked. Each impact can then be placed in one of a plurality of classes, including a first class in which each of the calculated impact parameters are within their associated desired ranges, a second class in which none of the calculated impact parameters are within their associated desired ranges, and a third class in which at least one of the calculated impact parameters is within its associated desired range and at least one of the calculated impact parameters is not within its associated desired range. Such a system could provide additional information to a trainer or other observer evaluating an athlete's performance.

Figure 7:
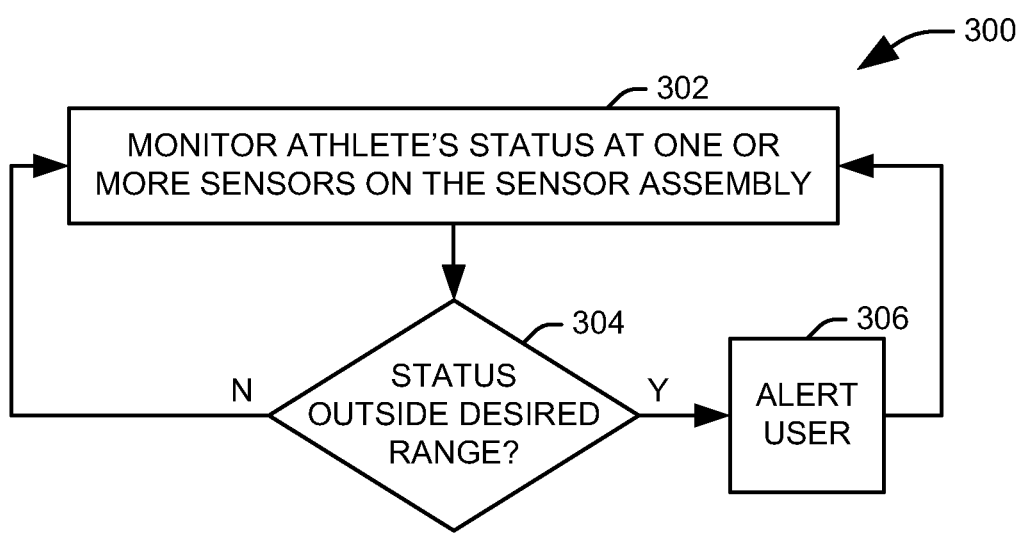
FIG. 7 illustrates a methodology for utilizing additional sensors, that is, sensors not directly used to measure impacts, placed on a sensor assembly in accordance with an aspect of the present invention to monitor a status of an athlete during an athletic event.

FIG. 7 illustrates a methodology 300 for utilizing additional sensors, that is, sensors not directly used to measure impacts, placed on a sensor assembly in accordance with an aspect of the present invention to monitor a status of an athlete during an athletic event. At 302, a status of the athlete is detected at a sensor on the sensor assembly. For example, the sensor assembly can include one or more sensors for detecting a temperature, sodium concentration, or location associated with the user. In one implementation, the sensor assembly includes an active radio frequency identification (RFID) device that works in concert with a tracking system at a location associated with the athletic event to provide a continuous updating of each athlete's position.

At 304, it is determined if the measured status is outside of a defined range. For example, it can be determined if the temperature or sodium concentration of the athlete is outside of a normal physiological range. Alternatively, it can be determined if the athlete has left the field of play or if the athlete has ventured into a restricted region of the field of play. If the measured status is within the defined range (N), the methodology 300 returns to 302 to continue monitoring the athlete's status. If the status is outside of the defined range (Y), a user is alerted of the deviation of the status from the defined range at 306, and the methodology 300 returns to 302 to continue monitoring the athlete's status.

It will be appreciated that the location tracking function of the sensor assembly could be useful in multiple contexts. It can often be difficult during team competitions to determine when a particular athlete of interest is on or off the field. A sensor assembly operating as described in FIG. 7 could give an observer an alert that their player of interest has entered the competition. For example, the parents of a high school football player could be alerted when their child is actively competing. The method 300 can also be used to determine where the player is at any particular time on the field of play. In one implementation, the status of the athlete could be updated regularly regardless of whether it exceeds the defined range, and a graphical interface could be provided with the position of all of the players represented by icons and the observer's player of interest having an icon of a different shape or color.

The methodology of FIG. 7 could also be used for rule enforcement. One common penalty that could be interpreted more readily with the methodology would be penalties relating to the number and position of players on the field. For example, penalties can be incurred for having too many players on the field or players at incorrect positions on the field in the sport of American football (e.g., players can be offside or too far from the line of scrimmage prior to a pass when not an eligible receiver). In one implementation, the players can be represented by icons that change color based on whether they are on or off the playing surface or according to the athlete's position on the field. This methodology could also be used by the individual team to prevent penalties.

In other applications, additional sensors placed on the sensor assembly of the impact monitoring system can be used to detect biometric data and trigger an event. Elite target shooters minimize body movement to improve accuracy. The impact monitoring system can be used as a trigger by varying pressure. It can also time the trigger to match biometrics such as heartbeat or breathing. Further, the sensor assembly can include some form of tactile indicator to improve the ability of handicapped athletes to participate. A hearing impaired athlete can be alerted to the start of an event such as a race by the transmission of a signal to the sensor assembly, with a component on the sensor assembly vibrating to alert the athlete of the starting signal. Thus, the athlete would not have to rely on vision to replace the sound of a starting signal. It would also be possible to transmit this signal to non-impaired athletes. This would allow a faster response to the start of a race versus listening for a signal and could improve performance.

Figure 8:
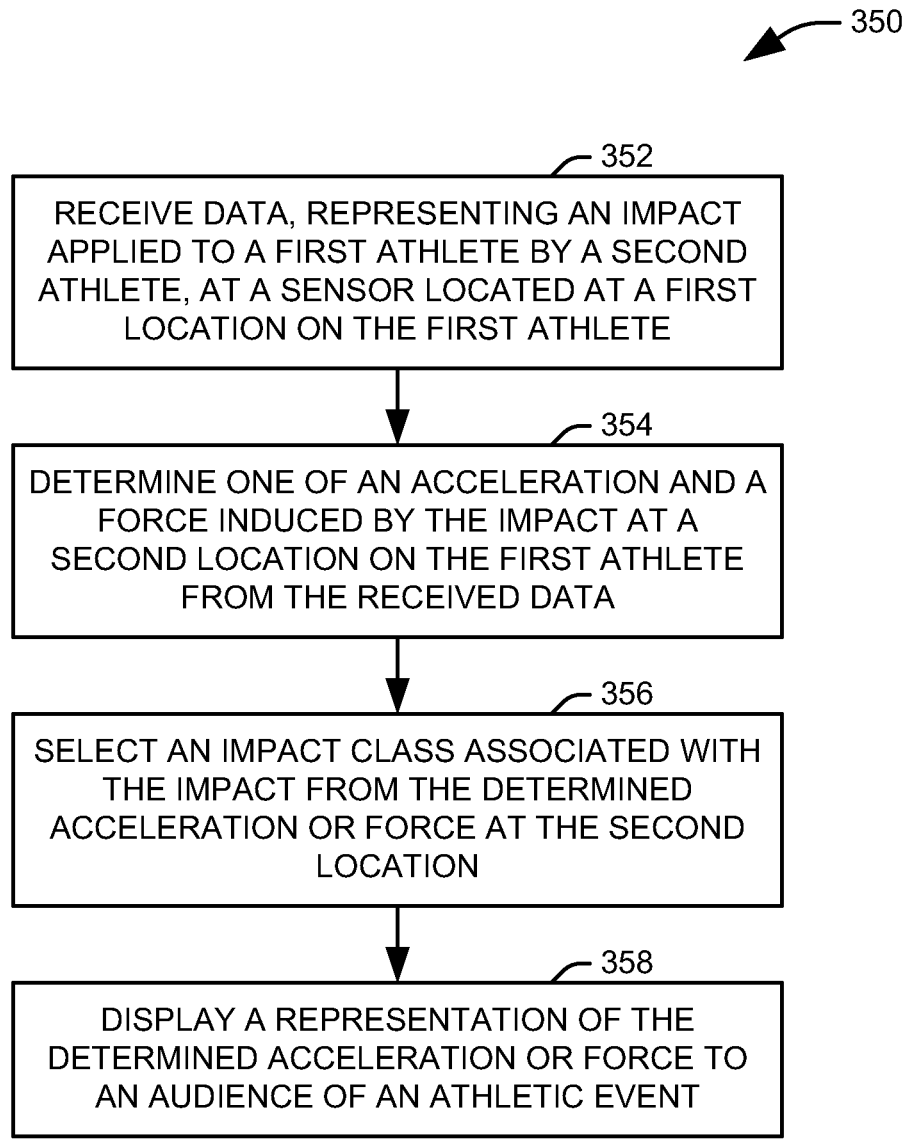
FIG. 8 illustrates a methodology for enhancing a presentation of an athletic event.

FIG. 8 illustrates a methodology 350 for enhancing a presentation of an athletic event in accordance with an aspect of the present invention. At 352, data, representing an impact applied to a first athlete by a second athlete, is received at a sensor located at a first location on the first athlete. For example, the sensor can be configured to measure at least one of a linear acceleration, an angular acceleration, an angular velocity, and an orientation of the head at the associated measurement point during the impact to the head, wherein the location of interest is remote from the associated measurement point.

At 354, one of an acceleration and a force at a second location, such as a center of gravity of the first athlete's head, on the first athlete induced by the impact is determined. For example, a projection of the acceleration or force at the second location along multiple axes can be determined, along with a magnitude of the acceleration or force. In one implementation, the acceleration or force can be represented as a time series, with the acceleration or force and the second location determined at multiple times within the impact. At 356, an impact class associated with the impact is selected from the determined acceleration or force at the second location. For example, the impact class can represent a particular type of strike that can be applied to the first athlete by the second athlete.

At 358, a representation of the determined one of the acceleration and the force at the second location on the first athlete is displayed to an audience of the athletic event. For example, displaying the representation of the determined one of the acceleration and the force at the second location comprises can include displaying a representation of the selected impact class. In one implementation, a graphic or text label can be shown to the audience to indicate the selected class. In an alternative implementation, the selected class can be displayed as an animation of the second athlete delivering an impact associated with the selected impact class, the first athlete receiving an impact of the selected impact class, or both. Alternatively, displaying the representation of the acceleration or force can include displaying a histogram of a plurality of impact classes, and updating the histogram each time one of the plurality of impact classes is selected to show that the second athlete has delivered another impact of the selected type.

In another implementation, the acceleration or force imparted to the first athlete can be shown as a cumulative sum, either numerically or graphically, with a slider or a chart. In one implementation, the cumulative sum can be shown as a reduction of a predetermined starting value each time the impact is received. In another implementation, the representation of the determined one of an acceleration and a force can include a parameter calculated as a function of the determined acceleration or force. In still another implementation, an indicator can be displayed to the audience when the determined acceleration or a force at the second location exceeds a threshold value. A running total of discrete impacts for which the threshold value is exceeded can be maintained for each athlete over a period of time and displayed to the audience.

Figure 9:
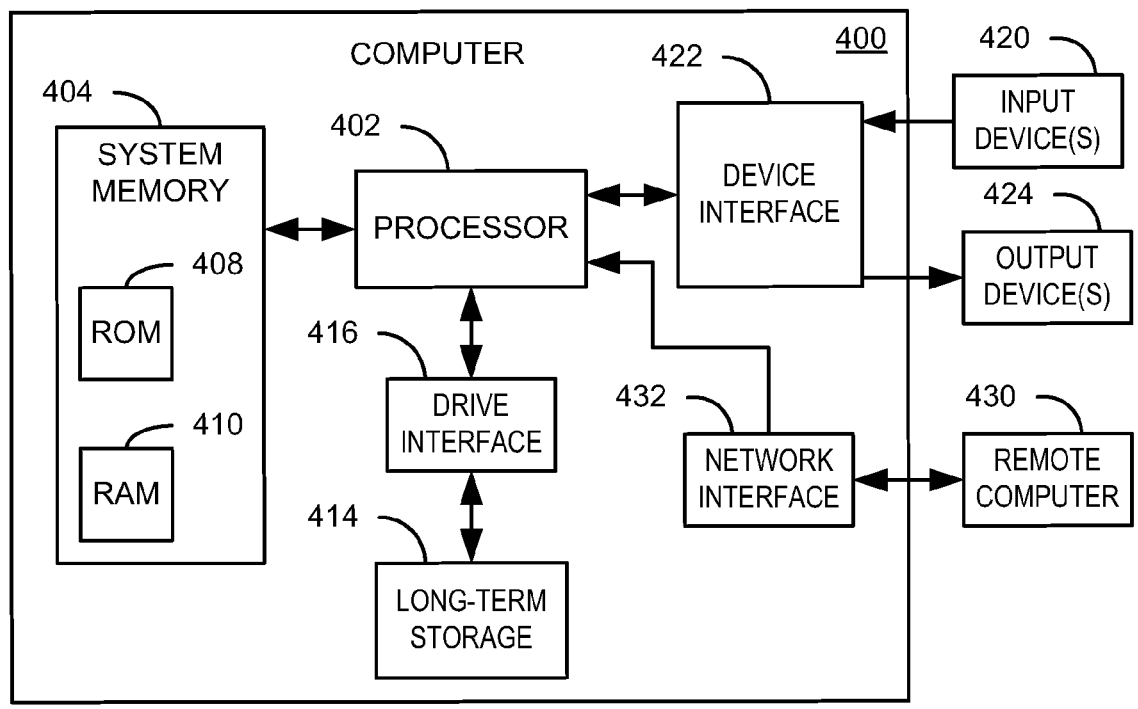
FIG. 9 illustrates a computer system that can be employed to implement systems and methods described herein, such as systems and methods based on computer executable instructions running on the computer system.

FIG. 9 illustrates a computer system 400 that can be employed to implement systems and methods described herein, such as based on computer executable instructions running on the computer system. The computer system 400 can be implemented on one or more general purpose networked computer systems, embedded computer systems, routers, switches, server devices, client devices, various intermediate devices/nodes and/or stand alone computer systems. Additionally, the computer system 400 can be implemented as part of the computer-aided engineering (CAE) tool running computer executable instructions to perform a method as described herein.

The computer system 400 includes a processor 402 and a system memory 404. Dual microprocessors and other multi-processor architectures can also be utilized as the processor 402. The processor 402 and system memory 404 can be coupled by any of several types of bus structures, including a memory bus or memory controller, a peripheral bus, and a local bus using any of a variety of bus architectures. The system memory 404 includes read only memory (ROM) 408 and random access memory (RAM) 410. A basic input/output system (BIOS) can reside in the ROM 408, generally containing the basic routines that help to transfer information between elements within the computer system 400, such as a reset or power-up.

The computer system 400 can include one or more types of long-term data storage 414, including a hard disk drive, a magnetic disk drive, (e.g., to read from or write to a removable disk), and an optical disk drive, (e.g., for reading a CD-ROM or DVD disk or to read from or write to other optical media). The long-term data storage can be connected to the processor 402 by a drive interface 416. The long-term storage components 414 provide nonvolatile storage of data, data structures, and computer-executable instructions for the computer system 400. A number of program modules may also be stored in one or more of the drives as well as in the RAM 410, including an operating system, one or more application programs, other program modules, and program data.

A user may enter commands and information into the computer system 400 through one or more input devices 420, such as a keyboard, a touchscreen, and/or a pointing device (e.g., a mouse). It will be appreciated that the one or more input devices 420 can include one or more sensor assemblies transmitting acceleration data to the computer 400 for further processing. These and other input devices are often connected to the processor 402 through a device interface 422. For example, the input devices can be connected to the system bus by one or more a parallel port, a serial port or a USB. One or more output device(s) 424, such as a visual display device or printer, can also be connected to the processor 402 via the device interface 422.

The computer system 400 may operate in a networked environment using logical connections (e.g., a local area network (LAN) or wide area network (WAN)) to one or more remote computers 430. A given remote computer 430 may be a workstation, a computer system, a router, a peer device, or other common network node, and typically includes many or all of the elements described relative to the computer system 400. The computer system 400 can communicate with the remote computers 430 via a network interface 432, such as a wired or wireless network interface card or modem. In a networked environment, application programs and program data depicted relative to the computer system 400, or portions thereof, may be stored in memory associated with the remote computers 430.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, the following is claimed:

1. A non-transitory computer readable medium storing executable instructions executable by an associated processor to perform a method for determining an acceleration at a location of interest within one of a user's head and neck, comprising:

receiving at least one of linear acceleration data, angular acceleration data, angular velocity data, and orientation data using a sensor assembly substantially rigidly attached to an ambient-accessible surface of the user's head at an associated position;

selecting one of a plurality of available time-varying functions representing the location of interest according to the received at least one of linear acceleration data, angular acceleration data, angular velocity data, and orientation data;

calculating an acceleration at the location of interest as a function of the data produced at the sensor assembly and the time-varying function representing the location of interest as a linear combination of at least the linear acceleration and a cross-product of the angular velocity and the time-varying velocity of the center of gravity; and providing the calculated acceleration at the location of interest to at least one of the user and an observer in a human-perceptible form.

2. The non-transitory computer readable medium of claim 1, wherein the sensor assembly is contained entirely within one of a mouth guard and a lip guard worn by the user, and calculating the acceleration at the location of interest comprises calculating the acceleration at the location of interest solely as a function of the data produced at the sensor assembly and the time-varying function representing the location of interest.

3. The non-transitory computer readable medium of claim 1, wherein the location of interest is a center of gravity of the head of the user.

4. The non-transitory computer readable medium of claim 1, wherein the location of interest is a location within one of a frontal lobe, parietal lobe, temporal lobe, occipital lobe, cerebellum, medulla oblongata, pons, thalamus, gyrus, fornix, amygdyla, hippocampus, cranium, facial bones, maxilla, mandible, cerebrospinal fluid, occipito-cervical junction, cervical spine, vertebral bodies, spinal cord, spinal nerves, spinal vessels, basal ganglia, peri-vascular spaces, septum, white-gray matter junctions, bridging veins, corpus callosum, fissure, cavity sinus, meninges, falx, dura, arachnoid, and pia matter of the user.

5. The non-transitory computer readable medium of claim 1, further comprising determining one of a Gadd Severity Index, a von Mises stress, and a Head Injury Criterion from the calculated acceleration.

6. The non-transitory computer readable medium of claim 1, further comprising calculating one of an impact force, a strain rate, and a loading rate at the location of interest from the calculated acceleration.

7. The non-transitory computer readable medium of claim 1, wherein the calculated acceleration is an angular acceleration, and further comprising calculating one of an angular jerk at the location of interest and an angular momentum of the user's head from the calculated acceleration.

8. The non-transitory computer readable medium of claim 1, further comprising calculating one of a Generalized Acceleration Model for Brain Injury Threshold, a relative motion damage measure, a dilatational damage measure, and a neck injury criterion from the calculated acceleration.

9. The non-transitory computer readable medium of claim 1, further comprising calculating one of a Head Impact Power parameter, a weighted principle component score, a strain energy, and a cumulative strain damage measure from the calculated acceleration.

10. The non-transitory computer readable medium of claim 1, further comprising calculating one of a peak pressure, a principal strain, a sheer stress, and a product of a strain and a strain rate from the calculated acceleration.

11. A system for characterizing an impact to a user comprising:

a sensor assembly configured to measure at least a linear acceleration and angular velocity of the sensor assembly;

a data transform component operatively connected to the sensor assembly and configured to represent a location of interest in one of the head and the neck of the user relative to a position of the sensor assembly as a time-varying function, including at least a time-varying velocity of the location of interest, and to calculate an acceleration at the location of interest as a linear combination of at least the linear acceleration and a cross-product of the angular velocity and the time-varying velocity of the location of interest; and a system interface configured to provide the calculated acceleration at the location of interest to a user in a human-perceptible form.

12. The system of claim 11, the sensor assembly comprising a plurality of linear accelerometers implemented as microelectromechanical (MEMS) systems.

13. The system of claim 11, the sensor assembly comprising a plurality of angular accelerometers implemented as MEMS systems.

14. The system of claim 11, the sensor assembly comprising a plurality of angular velocity sensors implemented as MEMS systems.

15. The system of claim 11, the sensor assembly comprising a plurality of angular position sensors implemented as MEMS systems.

16. The system of claim 11, the sensor assembly comprising a plurality and combination of linear accelerometers, angular accelerometers, angular velocity sensors and angular position sensors implemented as MEMS systems.

17. The system of claim 11, wherein the sensor assembly is implemented entirely in one of a mouth guard and a lip guard worn by the user, and the data transform component is configured to calculate the acceleration at the location of interest solely as a function of the data measured at the sensor assembly and the time-varying function representing the location of interest.

18. The system of claim 17, the one of the mouth guard and the lip guard being formed from multiple layers of material with the sensor assembly being mounted in one layer in an elongate pattern.

19. The system of claim 17, the one of the mouth guard and the lip guard comprising a wireless transmitter to provide the measured linear acceleration and angular velocity to the data transform component.

20. The system of claim 17, the one of the mouth guard and the lip guard comprising an on-board wired transmitter with data storage to provide the measured linear acceleration and angular velocity to the data transform component.

21. The system of claim 17, wherein the data transform component is mounted on a headpiece worn by the user, and the one of the mouth guard and the lip guard is connected to the data transform component via a wired connection.

22. The system of claim 11, the data transform component being configured to represent the location of interest relative to the sensor assembly as a time-varying function according to a model of the movement of a brain when exposed to various kinematics and kinetics.

23. The system of claim 11, the system interface comprising a remote warning device that alerts the user when the calculated acceleration exceeds a threshold value.

24. The system of claim 11, the system interface comprising an on-board warning device that alerts the user when the calculated acceleration exceeds a threshold value.

25. The system of claim 11, the data transform component being configured to select the time-varying function from one of a plurality of available time-varying functions representing the location of interest according to the measured linear acceleration and angular velocity.

26. A system for characterizing an impact to a head of an athlete during an athletic event comprising:

a sensor assembly encapsulated entirely within one of a mouth guard and a lip guard worn by the athlete and configured to measure at least the linear acceleration and the angular velocity of the sensor assembly;

a data transform component operatively connected to the sensor assembly and configured to calculate the acceleration at a center of gravity of the head solely from the measured at least one of the linear acceleration, angular velocity, angular acceleration, and orientation of the sensor assembly and a position of the sensor assembly relative to the center of gravity of the head, the data transform component being configured to represent a location of the center of gravity of the head relative to a position of the sensor assembly as a time-varying function comprising at least a time-varying velocity of the location of interest and calculate the acceleration at the center of gravity as a linear combination of at least the linear acceleration and a cross-product of the angular velocity and the time-varying velocity of the center of gravity; and a system interface configured to provide the calculated acceleration at the center of gravity to one of the athlete, a coach of the athlete, a family member of the athlete, a trainer of the athlete, an official associated with the athletic event, and an audience associated with the athletic event.

27. The system of claim 26, wherein the sensor assembly is configured to measure each of the linear acceleration, angular velocity, angular acceleration, and orientation of the sensor assembly.

28. The system of claim 26, the data transform component being configured to select the time-varying function from one of a plurality of available time-varying functions representing the center of gravity according to the measured at least one of linear acceleration, angular acceleration, angular velocity, and orientation.

* * * * *